United States Patent [19]

Reynolds

[11] 4,017,597
[45] Apr. 12, 1977

[54] UNITIZED SOLID PHASE IMMUNOASSAY KIT AND METHOD

[75] Inventor: John H. Reynolds, Baltimore, Md.

[73] Assignee: Monsanto Company, St. Louis, Mo.

[22] Filed: Oct. 30, 1974

[21] Appl. No.: 519,317

[52] U.S. Cl. .............................. 424/1.5; 23/230 B; 23/259; 195/103.5 R; 195/103.7; 424/12
[51] Int. Cl.² .................. A61k 43/00; G01N 33/00; A61B 10/00; C12K 1/04
[58] Field of Search ............ 424/1.5, 12; 23/230 B, 23/259, 253 R

[56] References Cited
UNITED STATES PATENTS

| 3,646,346 | 2/1972 | Catt ...................................... 424/12 |
| 3,790,663 | 2/1974 | Garrison et al. ..................... 424/12 |

OTHER PUBLICATIONS

Salmon, et al., Journal of Immunology, vol. 103, No. 1, July, 1969, pp. 129–137.

Primary Examiner—Benjamin R. Padgett
Assistant Examiner—Christine M. Nucker
Attorney, Agent, or Firm—John D. Upham; Joseph D. Kennedy; Scott J. Meyer

[57] ABSTRACT

A unitized solid phase kit for radioimmunoassay is disclosed. All of the necessary assay reagents are incorporated in a single tube wherein all phases of the assay procedure are performed, requiring only the addition of the patient's sample. Antibody is bound to the tube surface, while labelled antigen is also present but unbound. Storage in the absence of air and water results in the stabilization of the reagents such that the system can be stored for long periods.

33 Claims, 5 Drawing Figures

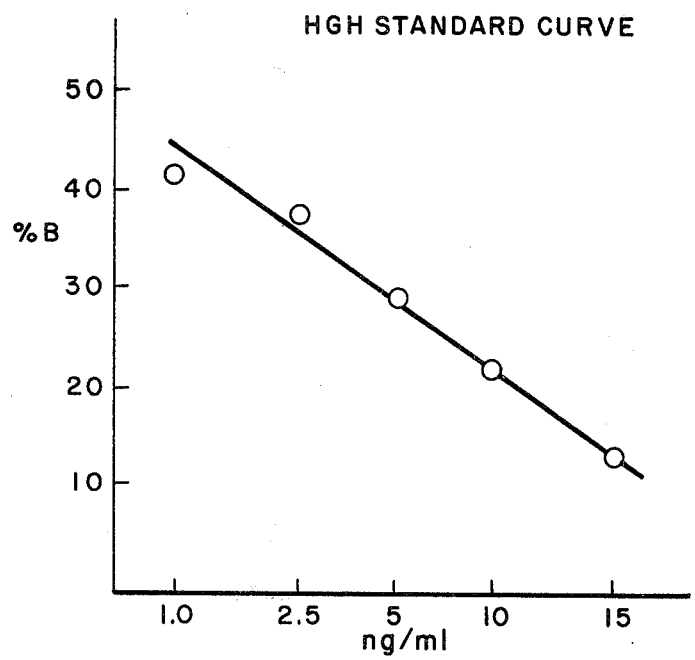
FIG. 3.
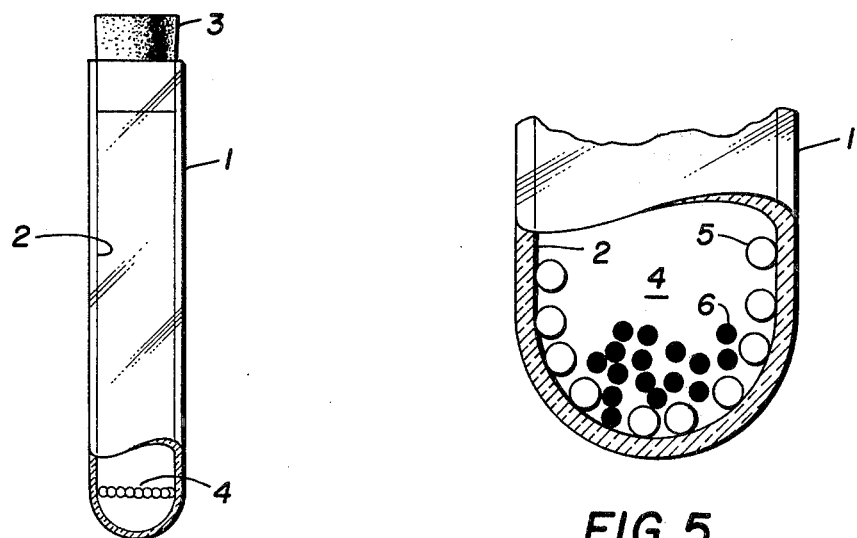
FIG. 4.
FIG. 5.

UNITIZED SOLID PHASE IMMUNOASSAY KIT AND METHOD

BACKGROUND OF THE INVENTION

Radioimmunoassay (also referred to as RIA) is a very sensitive method for the determination of antigens or antibodies, both qualitative and quantitative. Quantities down to $10^{-12}$ gram can be detected. The method is based upon the competition between radiolabelled and unlabelled antigen for a fixed and limited amount of antibody as described by R. Yalow et al in *J. Clin. Invest.*, 39, 1157 (1960). The amount of unlabelled antigen influences the distribution of the labelled antigen in antibody-bound and antibody-free labelled antigen. That is, the more unlabelled antigen which is present, the less labelled antigen gets the opportunity to combine with antibody.

In the accompanying drawings, FIGS. 1 to 3 are standard curves obtained by measuring standard concentrations of designated antigens in accordance with the present invention. FIGS. 4 and 5 illustrate a test tube assay means in accord with the present invention.

The term "kit" is employed herein to mean a collection of all or some of the chemicals, including the assay tubes, and instructions necessary to do a radioimmunoassay.

The term "antibody" or "antibodies" is employed to mean a group of serum proteins, also referred to as gamma globulins or immunoglobulins, that will specifically react with an antigen or hapten. Most of these antibodies belong to the IgG class, while the other classes are termed IgA, IgM, IgD, and IgE. It is also used herein to include certain binding proteins which recognize certain antigens, for example such protein for cyclic AMP and for cortisol.

The term "antigen" is employed herein to means a substance that will react with an antibody. Antigens are often characterized as capable of inducing the formation of an antibody and of reacting with that antibody. However, in the case of "haptens" it is necessary to be coupled to a carrier, such as, for example, inert adsorbing particles, synthetic peptides, or natural protein molecules, in order to induce antibody formation. Materials commonly employed as carriers include for example, the albumins (human, bovine, or rabbit), synthetic peptides (for example, polylysine), inert adsorbing particles (for example, dextran-coated charcoal) and polymers (for example, polyvinylpyrrolidone). However, haptens will in the absence of a carrier still react with antibodies and can be employed in the antigen-antibody reaction assays of the present invention either with or without carriers.

A necessary requirement for obtaining conclusive results from the radioimmunoassay method is the separation between the antibody-bound and antibody-free antigen. The development of various solid phase methods provides for rapid and efficient separation. In the solid phase type of assay, the antibody or antigen is bonded or fixed to an adsorbent, which facilitates separation or precipitation of bound or free fractions. See, for example K. J. Catt, U.S. 3,646,346 and K. Catt et al, *Science*, 158, 1570 (1967).

The solid phase antibody techniques make use of antibodies covalently bonded or fixed to insoluble polymers, convalently cross-linked, or physically adsorbed to a material, such as, for example, plastics, glass, or freshly deposited metals. The insoluble carriers or immunoadsorbents include bentonite particles, bromoethyl cellulose, the crosslinked dextrans (Sephadex), and beaded agarose (Sepharose).

While large amounts of antibodies are required in the solid phase antibody systems, they do have certain advantages. Binding of the antigen is rapid, virtually irreversible, and the two phases may be separated by simple decantation or low-speed centrifugation. In many instances antibody solutions can be reused for adsorption.

Polymerized antibodies, covalently cross-linked with ethyl chloroformate or glutaraldehyde, provide a practical and accurate method for assays. However, the method requires high speed centrifugation for precipitation of the antigen-antibody complex.

The solid-phase antibody method by bonding-adsorption includes the use of poly(tetrafluoroethylene-g-aminostyrene) ("Protapol") powder, poly(tetrafluoroethylene-g-isothicyanatostyrene) powder ("Protapol DI/1"), or polystyrene plastic tubes. The preparation of the antibody-coated discs or tubes may be affected by the pH, molarity, temperature, and protein concentration of the incubating solution. However the technique permits many determinations to be performed rapidly, and it is highly sensitive and reproducible.

One modification of the solid phase method, described by T. Goodfriend et al, *Immunochemistry*, 6, 484 (1969), uses an acrylamide gel that seems to entrap the antibody, but allows diffusion of low-molecular-weight antigens.

Additional information concerning radioimmunoassy is set forth in D. S. Shelly et al *Clin. Chem.*, 19, 146 (1973).

While the radioimmunoassay is a valuable technique in clinical practice, its use has been relatively limited. One possible reason for this is that it is difficult to set up, especially for a non-routine assay. In addition, commercial kits currently available are often unreliable, have poor stability and short shelf lives, are intricate and involved to the point of requiring skilled technicians for their operation.

It is an object of the present invention to provide a convenient means for the immunoassay of a component of the antibody antigen reaction. It is a further object to provide an improved kit for the radioimmunoassay method, free from the drawbacks of the prior art methods mentioned hereinabove.

It has surprisingly been found that the objects of the present invention can preferably be accomplished by introducing all of the reagents necessary for a radioimmunoassay into a single tube in a manner such that the antibody is bound to at least a part of the surface and the antigen is dispersed in solid form over at least a part of the surface but not bound thereto nor to the antibody.

The unitized solid phase radioimmunoassay kit offers several advantages over other radio-immunoassay kits. These include (1) elimination of the necessity for the technician to have to dilute to pipet radioactive material in combining the components in the assay procedure, which will result in increased safety for the technician, (2) the elimination of the necessity for the technician to have to dilute or pipet any material except the patient's sample which will result in a decreased chance of error and time spent doing the assay and (3) increased stability and storage life. Therefore, the unitized solid phase radioimmunoassay kit of the present invention offers potential savings in laboratory technician time, kit cost to a laboratory, and test cost to a patient.

SUMMARY OF THE INVENTION

The invention involves a means for use in the immunoassay of a component of the antigen-antibody reaction in which one of the components is bound to a solid surface, and one of the components is labelled and present in solid phase but unbound. One of the components may be adsorbed on a plastic surface while the other labelled component is dispersed in solid phase on the surface but not bound thereto, nor to the other components. In one aspect the invention involves storing the means under inert atmosphere prior to use, with achievement of good stability. In a more specific aspect, an antibody is adsorbed on the solid surface, and labelled antigen is present in solid phase but not bound to the surface. The invention further involves a method of preparing the assay means by coating and binding one component on at least part of a surface and then contacting the surface with labelled component in a manner to cause a dispersion of the labelled component in solid phase over at least part of the surface. In a more specific aspect, the method involves coating one component from solution onto the surface and applying a solution of the other component in labelled form and quickly freeze drying the solution. The invention also involves a method of assaying for antigen or antibody in which a surface is provided with one of the components bound thereto and a labelled component which is present in solid phase but unbound, contacting the surface with a solution containing the component to be determined, separating the solution from the surface, and measuring the labelled component on the surface or in the solution. The method in a more specific aspect involves providing a plastic test tube, well or cuvette, with antibody adsorbed on a portion of its internal surface, and having radioactively labelled antigen present in the test tube in solid form but not bound to its surface or to the antibody, contacting the internal surface with a solution containing the component to be determined to produce a two-phase system comprising a solid phase (test tube and material bound thereto) and a liquid phase, separating the two phases from each other, and measuring the radiation from at least one of said phases. In this procedure as usually employed the sample will contain antigen so that the amount of labelled component bound to the solid determined by competition between the labelled antigen and the antigen in the sample. In another aspect, the assay method can be considered as including the steps of preparing the assay means as described hereinabove.

The invention involves utilizing a bound component and an unbound solid labelled component in proximity as parts of an assay means, but avoiding premature reaction between the components. The assay, of course, depends upon the fact that the components will react, e.g. a bound antibody and a labelled antigen. It has been discovered that it is feasible to have the labelled antigen present in solid state on the same surface as the bound antibody without obtaining bonding or reaction such as to prevent a proper assay. The fact that such components can be pre-packaged together into an assay means adds greatly to the convenience of use of such assay means. For use, it is only necessary to add the patient's sample containing the component to be determined. After an appropriate incubation period, a complete and rapid separation of the bound component, both labelled and unlabelled, from the free component is effected by decantation and washing, so that the activity of the solid phase can be measured, the value of the activity being a function of the concentration of said component to be determined in the sample.

It has been found that an ordinary relatively smooth and impervious solid surface can be employed in the assay means, such as molded plastic surfaces, for example surfaces as found in ordinary plastic laboratory test tubes, and that a liquid can be conveniently separated from the surface by simple decantation without need for centrifugation, aspiration or similar means. Procedures used in preparing the assay means make it possible to have the labelled component in solid form on the surface without obtaining reaction, particularly procedures in which the surface is pre-cooled to low temperatures, such as near freezing, prior to contact with the solution of the labelled component, and in which the solution is then quickly frozen, as for example by quickly cooling to temperatures of $-50°$ C or below. Both the low temperature and the quick conversion to solid form contribute to avoiding reaction. After lyophilization, the labelled component is present as a solid dispersed over the surface of the test tube. There may be some attraction between the surface and the labelled component, but the labelled component is unbound in the sense that it can readily be removed from the surface by application of liquids, such as sample solution.

DETAILED DESCRIPTION OF THE INVENTION

Figure 1:
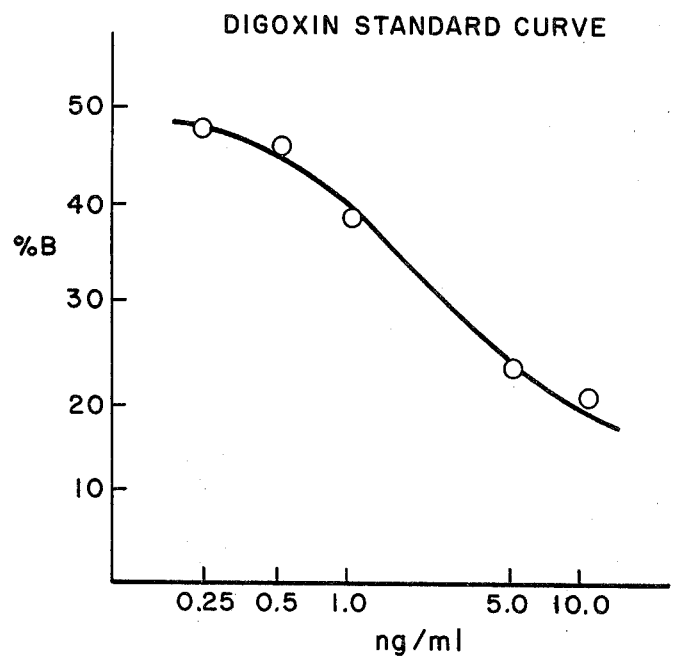

The unitized solid phase radioimmunoassay kit of the present invention is particularly suited for the determination of either component of antigen-antibody reaction. While the invention, for convenience, may be more particularly illustrated with respect to the determination of the antigen component, it will be understood that the procedures are similarly applicable to determinations of antibodies. Similarly, the test tube will be used for purposes of exemplification of solid surfaces of the binding material, but other shapes of surfaces can be used.

In carrying out the preparation sequence of the present invention, the following procedure can be employed. The interior surface of a test tube of material capable of binding antibodies against the antigen to be determined is contacted with a dilute solution of the antibodies (antiserum). The liquid is removed by aspiration and the tubes are washed successively with a dilute solution of sodium bicarbonate buffer, a dilute solution containing sodium phosphate, and a small amount of pure protein to reduce the nonspecific binding of the antigen, and finally a dilute solution of sodium phosphate buffer.

The term "pure protein" or simply "protein" as employed herein is intended to include proteins and polypeptides that are free of contamination, and it is good practice to use such pure material to avoid unnecessary interfering factors.

Following the completion of the washings, the tubes are cooled to a temperature between about $-10°$ C and about $5°$ C and a dilute solution of the radioactive antigen is added thereto. The contents are frozen at solid carbon dioxide temperature, approximately $-78°$ C, very rapidly, preferably within 5 to 15 seconds. Lyophilization of the tubes for a period of about 8 to 16 hours completes the preparation sequence. The tubes can be safely stored in an inert and moisture-free atmosphere, such as, for example, nitrogen, for periods of a number of months or more without any significant loss of activity. The temperature at which the tubes can be safely stored ranges from below 0° C to about 40° C, or even higher. A convenient temperature range, however, is between about 4° C and about 25° C.

The unitized solid phase radioimmunoassay kit of the present invention is stable for a period of at least five months, as determined by the slope of the standard curve at the time tests were discontinued. The slope of the standard curve decreases over the long storage period, but never to a point that the tubes are no longer useful for a good assay. For example, in the case of digoxin, a standard serum reference sample of 3.3 nanograms per milliliter was assayed each week over a two-month period. The average value obtained for this period was 3.1 nanograms per milliliter with a standard deviation of 0.3 and a coefficient of variance of 9.6 percent. Of course, allowances are made for normal radioactive decay.

The antigen may be labelled in a conventional manner with any labelling material suitable for use in immunoassay methods, such as, for example, radioactive isotopes, enzymes, fluorescent groups, and spin-label groups. Isotopes commonly employed for this purpose include iodine-125 ($I^{125}$), iodine-131 ($I^{131}$), carbon-14 ($C^{14}$), and hydrogen-3 ($H^3$), commonly known as tritium, A particularly suitable radioactive isotope label is $I^{125}$. It has a half life of about 60 days, and it readily reacts with most antigens. It also has a higher specific activity than either $H^3$, $C^{14}$, or $I^{131}$. Furthermore, it has a lower gamma energy than does $I^{131}$, and the absence of beta-radiation diminishes the potential for autodistinction of the labelled antigen.

Some assays of proven clinical value which are representative of those for which the solid phase, single tube, single step system of the present invention is suitable are listed in Table I.

TABLE I.

SOME ASSAYS OF PROVEN CLINICAL VALUE

| | Peptide and Protein Hormones |
|---|---|
| Anterior pituitary | Luteinizing hormone (LH); follicle-stimulating hormone (FSH); thyroid-stimulating hormone (TSH); human growth hormone (HGH); prolactin; corticotrophin (ACTH) |
| Posterior pituitary | Arginine-vasopressin (AVP) |
| Parathyroid | Parathyroid hormone (PTH) |
| Pancrease | Insulin |
| Placenta | Human placental lactogen (HPL); human chorionic gonadotrophin (HCG) |
| Others | Angiotensin I and II; renin; gastrin |
| | Other Peptides and Proteins |
| Plasma proteins | Immunoglobulin (IgE); fibrinogen; other clotting factors |
| microbial antigens | Hepatitis-associated antigens |
| Specific tumor antigens | alpha-Fetoprotein; carcino-embryonic antigen |
| | Hapten Hormones |
| Thyroid | Thyroxine ($T_4$); triiodothyromine ($T_3$) |
| Adrenal | Cortisol deoxycorticosterone; aldosterone; |
| Gonadal | Testosterone; progesterone; various estrogens |
| | Other Haptens |
| Drugs | Digoxin; morphine; cannabis; diphenylhydantoin |
| Others | Folic acid; cyclic-adenosine monophosphate (C-AMP); vitamin $B_{12}$; vitamin D |

The present invention also encompasses a method of use. This method comprises adding the unlabelled antigen complex solutions and the standard reference sample solutions to the assay tubes, incubating at the desired temperature for the desired length of time, washing, removing the solutions, and counting the radioactivity of the bound labelled antigen sample in an analytic gamma spectrometer. Alternatively, the activity of the solution is counted. The number of counts per time of standard tubes is converted into percent of bond (%B) antigen -$I^{125}$ based on the total amount of antigen. -$I^{125}$ added to the tubes. The percentages obtained are plotted to form the standard curve, such as those shown in FIGS. 1, 2, and 3. From the standard curve the concentration of antigen in the unknown sample is easily determined by direct comparison.

Figure 2:
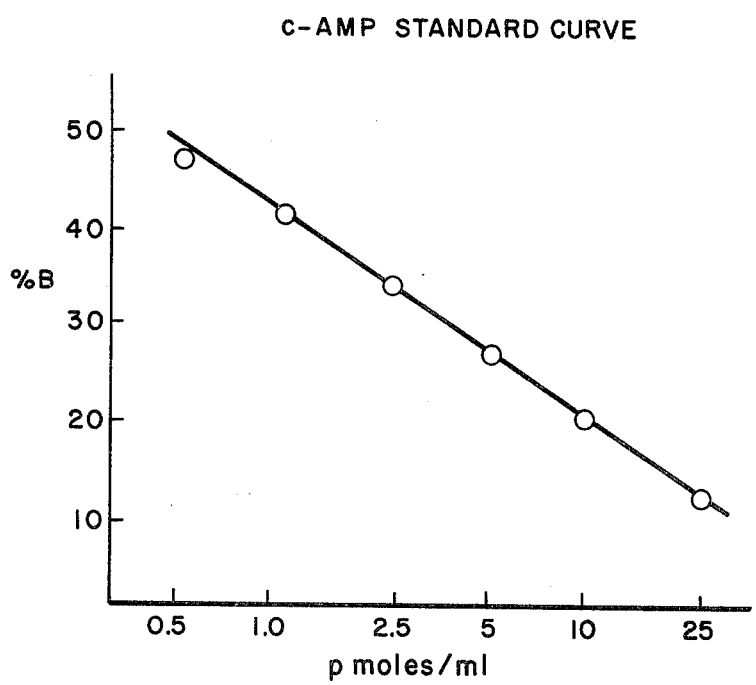

In the accompanying drawings there are shown examples of standard curves which were determined in the practice of the present invention. The following is a brief description of the various figures:

FIG. 1 shows a standard curve obtained by plotting the percent of bound digoxin-$I^{125}$ along the ordinate against the logarithm of the concentration of digoxin in nanograms per milliliter along the abscissa (see Example 1 below);

FIG. 2 shows a standard curve obtained by plotting the percent of bound (cyclic-adenosine monophosphate)-$I^{125}$ [(C-AMP)-$I^{125}$] along the ordinate against the logarithm of the concentration of C-AMP in picomoles per milliliter along the abscissa (see Example 2 below); and FIG. 3 shows a standard curve obtained by plotting the percent of bound (human growth hormone)-$I^{125}$[(HGH)-$I^{125}$] along the ordinate against the logarithm of the concentration of HGH in nanograms per milliliter along the abscissa (see Example 3 below).

In general, the assay means of the present invention depends upon competition between a labelled component and a component of the sample for binding by a component which is bound to the solid surface. Therefore, the bound component will be present in an amount insufficient to bind all of the sample component and labelled component. The proper amounts of the components for such relationship can be readily determined by trial and error procedures. For convenient reading, particularly with $I^{125}$, radiation in the range of 2000 to 60,000 counts per minute (CPM) is appropriate. An amount of labelled component of 10,000 CPM at the start of the assay provides suitable flexibility, and it often may be desireable to use much higher amounts in preparing the assay tubes in order to allow for radioactive decay over a storage period. The radioactively labelled component in solution can be diluted so that about 1/10 ml. contains the proper amount for the desired CPM, and the 1/10 ml. can then be added to the test tube for coating purposes. The amount of bound component in the test tube can be adjusted so that it will bind a substantial fraction of the labelled component, say 40 to 60%, although other amounts can be used, such as amounts to bind 20 to 80%, or even broader ranges. An amount to bind about 50% of the labelled component permits flexibility in use of the assay procedure. For digoxin determinations, for example, about 1 picogram of digoxin antibody bound in the test tube is an appropriate amount. The assay procedure will then ordinarily be used for assays of samples having concentrations of the unknown component to give percentages of bound labelled component in the range of 10 to 20 up to 50 or so percent, depending upon the particular unknown component and the breadth of the range at which it usually occurs in the biological or other fluid being assayed. If desired, the fluid assayed can be diluted or concentrated for adjustment of concentration for convenient determination. However, for example, the normal serum range for digoxin in digitalized patients is between 0.8 and 2.4 nanograms per ml. and the toxic range is 2.4 to 8.5 nanograms per ml., so an effective assay range of 0.2 to 10 nanograms per ml. is convenient.

In preparing the assay means herein, definite fixed amounts of the components will be utilized, and it will be desirable to use standard procedures for the preparations in order to obtain assay results which are consistent for comparison with standards, etc., as is well understood by those versed in the field. Thus after appropriate amounts are determined, the same determined amounts should be provided for a particular set of assay tubes. Such preparations can be accomplished in accordance with the procedures illustrated herein. It is not necessary to identify the amounts numerically, as by analysis, as such amounts can be fixed by use of particular preparation techniques. For example, approximately identical quantities of antibody can be provided in a set of tubes by introducing the same quantity of dilute antibody serum, incubating for a standard time, aspirating, and washing. The aspiration of the serum leaves a film behind and the amount of antibody thus adsorbed is ordinarily so small that an antibody serum of sufficient concentration can be used so that the aspirated serum can be used to coat additional tubes. The labelled component when added in a minute amount of liquid is ordinarily introduced so that it is confined to the part of the tube previously coated with antibody. However, the labelled component can be present on a different part of the tube or on some other surface, so long as it is present and available for contact with sample solution when introduced into the tube.

In procedures described herein, buffering, protein coating solutions, and other common expedients known to the art are employed, but definition of such aspects is not essential to the invention. Appropriate buffering and similar solutions will vary with the particular antibody-antigen system, as well understood by those in the art. The purpose of using protein coatings, such as serum albumin, is to limit non-specific binding of unbound components during the assay, but this individual feature by itself is old and well understood by those in the art. Moreover, allowances can be made for non-specific binding in calibrating the assays. In addition, some components, for example digoxin, have very little tendency to adsorb on plastic surfaces, and there is little benefit in such cases in the use of coatings to prevent non-specific binding. The protein or other masking coatings employed may substantially cover the surfaces involved but this is not essential as the object is to reduce non-specific binding and it is not necessary to completely eliminate it. Moreover, when general reference is made herein to materials bound to or in contact with surfaces of test tubes or other substrates, it will be understood that there may be intermediate layers or parts thereof or particles between the surface and the materials referred to, and a bare surface or one containing various layers will still be referred to as a surface.

The buffering agents, wash solutions, etc. utilized herein are employed as biologically acceptable carriers and the like which preserve the effectiveness and character of the components involved, in a manner similar to use of pharmaceutically acceptable carriers, and mildly basic buffering agents in general are often suitable for such uses herein.

The labelled component in the present invention is generally introduced by the quick freezing and lyophilization technique described herein. This is a very suitable procedure for introducing the labelled component without reacting it. However, any procedures can be used which result in the presence of the labelled component in solid unbound and unreacted form. In theory it could be added as a solid powder, but this would not be practical because of the problems in measuring very minute amounts. Also the labelled component can be introduced dissolved in a low boiling solvent which is then quickly evaporated. Depending upon the activity of the particular antibody-antigen reaction, the evaporation may be rapid enough to avoid substantial reaction. Vacuum can suitably be employed to assist in the evaporation. Alcohols may serve as solvent in such procedures, provided solubility is sufficient and denaturation does not result. In general, low boiling solvents which dissolve the labelled component without changing its character can be employed. However, it will ordinarily be more convenient and satisfactory to employ quick freezing and lyophilization techniques as described herein.

It has been found that the assay means described herein with both an antibody and antigen present in solid state and with one of them being labelled, are not only convenient for use and capable of advance preparation, but are amazingly stable upon storage for extended periods. It is considered feasible to store such means for up to three or six months or more in inert atmosphere, e.g. under nitrogen, and in absence of moisture. It has been found also that low temperatures are not necessary for such stability, as temperatures such as 25° C, and 37° C, have been found suitable for storage. Thus by vacuum packing, hermetic sealing etc. it is feasible to ship the assay means of the present invention in unrefrigerated packages, and retain effectiveness despite possible long delays in transit etc. As a precaution it may be desirable to keep the assay means refrigerated, possibly near the freezing point or about 4° C., but the ordinary temperature stability will still be advantageous because of possible exposure to such temperatures prior to use, or the economic advantage of being able to ship without refrigeration. The assay tubes can be individually sealed under vacuum or nitrogen, employing sealing or closure means commonly used to protect contents of test tubes or ampules from the atmosphere. The individual tubes can then suitably be packaged in a sealed container which can contain, in addition to the assay tubes, antigen or antibody standards and instructions for use. Rubber or similar stoppers can, for example, be used to seal the tubes hermetically. One convenient type of stopper is a slotted rubber stopper which can be fitted into the tube so that the slot or slots provide access to the interior. A set of tubes containing such stoppers can be placed in containers under nitrogen, and then a ram shoves the stoppers in completely to form a hermetic seal, and the container can also be sealed under nitrogen.

Much of the disclosure herein is particularly concerned with a system in which the antibody is bound to an insoluble surface, and the antigen is labelled, and the amount of antigen in an unknown sample is assayed. However the invention also includes means and methods for other determinations, as for example, a means having antigen bound to a surface and labelled antibody in solid form but unbound, and use of the means for assay of antibody in a sample. For example, human growth hormone (HGH) can be coated on a polystyrene tube from solution in accordance with procedures described herein for coating antibodies, and antibodies obtained from HGH antiserum can be radioiodinated and introduced into the test tube in accordance with the quick freezing and lyophilization procedures described herein, and the test tube will then contain the HGH bound to the surface of the tube, and the unbound solid labelled antibody.

The assay means of the present invention is generally used to assay the component of the antigen-antibody reaction which is labelled, but it can also be used to measure the other component. For example, with bound antibody and labelled antigen, a sample of unknown antibody can be introduced and the labelled antigen will then distribute itself over the bound antibody and the free antibody, and the solid and liquid phases can be separated and the label of at least one measured. In this procedure the concentrations will differ in that the amount of labelled antigen should be insufficient to react with all the antibody. If the assay means has been prepared so that the antibody is sufficient to bind 50% of the labelled antigen, the antibody sample can be employed at a dilution such that its antibody is in excess of the bound antibody of the assay means, and the labelled antigen will then be insufficient to react with all antibody which is the desired condition.

Similarly, when antigen is bound and labelled antibody present, the means can be utilized to assay antigen in a sample with the labelled antibody distributing itself over the bound antigen and free antigen, with separation and measurement procedures as described above. The labelled antibody will be employed in amount insufficient to react with all of the antigen present in bound and free forms.

The present invention also includes procedures in which a bound component is combined with the same component labelled but unbound, and used to measure the opposite component in a sample. For example, antibody can be coated on a test tube and the same radioactively labelled antibody can then be added by the quick freezing and lyophilization procedure described herein. A sample serum containing the corresponding antigen can then be introduced, and the antigen will react with the bound antibody, as well as with the labelled antibody, thereby immobilizing part of the labelled antibody by binding it indirectly to the test tube surface, and permitting the usual separation of solid and liquid phases and determination of the labelled antibody in one or both. This type of procedure may be particularly useful when an antigen cannot conveniently be isolated and radioactively labelled, and may find use in assay of such antigens as hepatitis antigen, etc. Similarly, this type of procedure can be employed with bound antigen and free labelled antigen to measure the amount of antigen in a sample. In such procedures both the bound and labelled components of the assay means should be in excess of amounts needed to react with the component in the sample.

In the preparations and assays of the present invention it will be convenient to employ aqueous media containing the specified components for solubility considerations and the fact that biological sample fluids and the like are generally aqueous. However other liquids can be employed provided the components are soluble therein and that there is no undue reaction or interference with the components.

In the present invention one of the components of the antigen-antibody reaction is bound to the surface of an insoluble solid, which is ordinarily a water insoluble solid as aqueous media is generally employed. The binding can be chemical, physical-chemical, or physical, and can be by covalent chemical bonds or by adsorption, and any insoluble solid material capable of such bonding can be employed, for example such surfaces as freshly deposited metals, such as chromium and tantalum, glass, and polymeric plastics, including hydrocarbon polymers and polyolefins such as polystyrene, polyethylene, polypropylene, and such polymers as nitrocellulose, copolymers of acrylonitrile with styrene such as poly (styrene-co-acrylonitrile), polytetrafluoroethylene, polytetrafluoroethylene-styrene, polytetrafluoroethylene-isothio-cyanatostyrene, etc. It has been found that the simple polymeric plastic tubes such as polystyrene tubes provide sufficient binding and other plastics similarly adsorb antibodies, so there is generally no need to utilize materials having reactive groups such as the -NCS groups on the isothiocyanatostyrene grafted polytetrafluoroethylene, but such materials with reactive groups can be employed if desired. Metals may give poor results if the surface is covered with an oxide film. Glass materials may require special treatment or selection as in use of quartz glass or coupling agents or the like to provide suitable binding.

The unitized solid phase radioimmunoassay kit of the present invention can be modified to produce a completely automatic design. For example, instead of individual tubes, a continuous plastic belt could be used to store the assay reagents in depressed spots on the belt, the samples and standards automatically spotted on the belt, and the belt fed through an incubation station, a washing station, and a counter with automatic printout of results.

The following examples will serve to illustrate the preparation and method of use of the unitized solid phase radioimmunoassay kit of the present invention.

EXAMPLE 1

UNITIZED SOLID PHASE RADIOIMMUNOASSAY KIT FOR DIGOXIN

Digoxin antiserum was purchased from Collaboraive Research, Waltham, Massachusetts; iodinated digoxin derivative was obtained from Schwartz-Mann, Orangeburg, New Jersey; and the polystyrene test tubes (No. 2052) were obtained from Falcon Plastics, Los Angeles, California.

A small portion of the inside of polystyrene tubes was coated by introducing 200 microliters of digoxin antiserum (diluted 1:5000 with a solution of 0.05 molar sodium bicarbonate, pH 9.6) into the bottom and incubating for between one to three hours at a temperature between about 20° C and about 30° C. After aspiration of the liquid, the tubes were washed successively with the bicarbonate buffer, a 0.05 molar sodium phosphate, 0.02 molar disodium salt of ethylenediaminetetracetic acid ($Na_2EDTA$) solution, containing 1 percent bovine serum albumin to reduce the non-specific binding of the antigen, and finally with 0.05 molar sodium phosphate buffer alone. The iodinated derivative of digoxin was diluted 1:5 in the phosphate buffer and 100 microliters (7,200 counts per minute) added to the tubes, previously cooled to about 0° C in an ice bath. The contents were immediately frozen (within 5 to 15 seconds) in solid carbon dioxide. The tubes were lyophilized for a period of 8 to 16 hours and finally stored in the absence of air and water under phosphorous pentoxide and nitrogen in small desiccators, one set at 4° C and another at 25° C, neither of which showed any significant loss of utility after eight weeks, as determined by the slope of the standard curve and the reproducibity of a reference sample over this period.

At the time of use the tubes were brought to room temperature, if necessary. Standard digoxin samples (unlabelled) and the standard reference sample containing 3.3 nanograms of digoxin per milliliter were added to the tubes. The tubes were thereafter incubated at about 25° C for about one hour, washed with phosphate buffer, and finally counted in an analytic gamma spectrometer.

On accompanying drawing FIG. 1 there is shown a standard curve obtained immediately after the tubes were dry on the lyophilizer. The number of counts per time of standard tubes was determined and converted into percent of bound (%B) digoxin-$I^{125}$ based on the total amount of digoxin-$I^{125}$ added to the tubes. The percentages obtained were plotted along the ordinate against the logarithm of the concentration of digoxin in standards on the abscissa to form the curve. From this standard curve the concentration of digoxin in an unknown sample may be easily determined.

A 3.3 ng/ml sample of digoxin was assayed weekly for eight weeks. The mean of the determined values was 3.1 ng/ml with a standard deviation of 0.3.

EXAMPLE 2

UNITIZED SOLID PHASE RADIOIMMUNOASSAY KIT FOR CYCLIC-ADENOSINE MONOPHOSPHATE (c-AMP)

Both the c-AMP antiserum and iodinated c-AMP were obtained from Biotek Co., St. Louis, Missouri.

The procedures and conditions of Example 1 above were employed except that the assay buffer was 0.02 molar sodium acetate, pH 6.4. The system was stored for three months with no significant loss of utility. A 1/100 diluted urine sample was assayed weekly over a period of 10 weeks. The means was 7.26 ng/ml with a standard error of 0.43.

The standard curve shown in FIG. 2 was obtained in the manner of FIG. 1 except the concentration of c-AMP along the abscissa is stated in picomoles per milliliter.

EXAMPLE 3 UNITIZED SOLID PHASE RADIOIMMUNOASSAY KIT FOR HUMAN GROWTH HORMONE (HGH)

The HGH antiserum was obtained from Biotek Co., St. Louis, Missouri. Iodination of HGH was effected according to standard procedures. See, for example, W. M. Hunter and F. C. Greenwood, *Nature*, 194, 495 (1962).

Following the procedures and conditions of Example 1 above, the kit for HGH was prepared and stored for five months without any significant loss of utility. The FIG. 3 shows a standard curve obtained in analogy with FIG. 1. A single human serum sample was assayed weekly for 8 weeks. The mean value was 2.24 with a standard error of 0.14.

EXAMPLE 4

RADIOIMMUNOASSAY OF HUMAN GROWTH HORMONE ON QUARTZ SURFACE

Fused quartz rods (1 × 20 mm) were cleaned in hot 50% nitric acid for a period of two hours. The excess acid was washed off with deionized water and air-dried. Each rod was introduced into a 6 × 50 mm glass test tube to which was added diluted (1/500 with 0.05 M sodium bicarbonate, pH 9.6) anti-human growth hormone serum to cover the rods. Incubation was allowed to occur for two hours at 25°. The antiserum then was aspirated and the rods thoroughly washed with bicarbonate, buffer and coated with bovine serum albumin as in Example 1. The remainder of the assay was performed as in Example 3 using polystyrene tubes. The quartz rod is placed in the tube, along with iodinated HGH, and the HGH in samples and standards is measured. A suitable standard curve was obtained from the graph of the percent labeled growth hormone bound versus the logarithm of the concentration of the growth hormone standards. While for convenience, a quartz rod was utilized here, the procedure illustrates that quartz tubes could be used to bind the antibody and the labelled antigen could then be placed in the tube in solid form by the coating and lyophilization techniques described herein, and the tubes could be stored and subsequently used for assays as described herein.

EXAMPLE 5

RADIOIMMUNOASSAY OF HUMAN GROWTH HORMONE USING SANDWICH TECHNIQUES

Anti-human growth hormone serum (diluted 1/500 with 0.05 M sodium bicarbonte, pH 9.6) was pipetted into the bottom of a 12 × 75 mm polystyrene plastic tube. The antibody was allowed to adsorb to the surface of the tube for a period of two hours at 24°. Radioiodinated ($125_I$) purified anti-human growth hormone (100 ul, 10,800 cpm) was pipetted into the bottom of the tube at 0°, immediately frozen at −70° and lyophilized. The tubes then were ready for assay of human growth hormone in human serum.

To these tubes were added human growth hormone standards in whole human serum of 100, 10 and 1 ng. The antigen-antibody reaction was allowed to take place for 18 hours at 24°. The tubes were washed with water three times and counted in a gamma spectrometer. A suitable standard curve was generated. The hormone concentration is a logarithmic function of the radioiodinated hormone bound to the tube.

An assay tube as employed in the present invention is illustrated in FIG. 4. The illustration is of the tube as it exists prior to adding sample, and containing the antibody and labelled antigen in solid state. The tube 1 has walls 2 and contains a stopper 3 and a reaction zone 4. If desired, the stopper can be slotted (not illustrated) as described herein. The reaction zone is illustrated in exploded view, FIG. 5, in which the circles 5 represent antiboides bound to the wall 2, and solid dots 6 represent labelled antigens generally disposed in the reaction zone 4 but not bound to the walls of the tube. As an alternate, the antigen can be bound to the surface, and labelled antigen can be disposed in unbound form in the tube. In another combination, bound antibody can be present with labelled, unbound antibody, or bound antigen, with labelled, unbound antigen. It is also possible to have the components present in different locations in the tube, for example to have the antibody bound to the side walls of the tube, and the labelled antigen on the bottom of the tube, but there is no need to have such separate locations, and the tube as illustrated can be readily prepared. The tube when stored contains dry nitrogen or other inert dry gas, or is under vacuum.

While the invention has been described with respect to various specific examples and embodiments thereof, it is to be understood that the invention is not limited thereto and that it can be variously practiced within the scope of the following claims.

What is claimed is:

1. A means for use in the immunoassay of a component of the antigen-antibody reaction comprising a surface within a receptacle to at least a part of which one of the components in solid form is bound and in proximity to which the other component is present in labelled and in solid form but not bound, said components being present within said receptacle under conditions substantially impervious to the ambient atmosphere.

2. The means of claim 1 in which an antibody is bound to the surface and antigen is labelled and unbound.

3. A means for use in radioimmunoassay comprising a surface within a receptacle having an antibody in solid form bound to at least a part thereof and radioactively labelled antigen in solid form dispersed over a portion thereof but not bound thereto, said antigen and antibody being present within said receptacle under conditions substantially impervious to the ambient atmosphere.

4. A means for radioimmunoassay comprising a plastic assay tube having a relatively impermeable smooth surface and having antibody in solid state bound to a part of its interior surface and containing radioactively-labelled antigen in proximity thereto in solid state but not bound to the surface, said antigen and antibody being present within said tube under conditions substantially impervious to the ambient atmosphere.

5. The means of claim 4 in which the antibody is present in amount sufficient to bind 40 to 60% of the labelled antigen.

6. The means of claim 4 in which the tube contains an inert, moisture-free atmosphere and is hermetically sealed.

7. The means of claim 3 stored under a mositure-free nitrogen atmosphere.

8. The means of claim 2 in which antibody is adsorbed on a plastic polymeric surface.

9. The means of claim 8 in which a relatively impermeable smooth polyolefinic surface is employed.

10. The means of claim 9 in which a polystyrene surface is employed.

11. The means of claim 2 in which the antigen is digoxin and the antibody is antibody to digoxin.

12. The means of claim 2 in which the antigen is human growth hormone and the antibody is antibody to human growth hormone.

13. The means of claim 2 in which the antigen is cyclic adenosine monophosphate and the antibody is antibody to cyclic adenosine monophosphate.

14. A method of preparing an immunoassay means which comprises coating and binding one of the components of an antigen-antibody reaction to at least part of a surface within a receptacle, and contacting the surface with the other component in labelled form in a manner to cause a dispersion of such component in solid form over at least part of the surface but not bound thereto nor to the other component, said components being present within said receptacle under conditions substantially impervious to the ambient atmosphere.

15. Method of claim 14 in which a test tube of water insoluble impervious polymeric material is coated with antibody from aqueous solution followed by removal of excess solution and washing, and then an aqueous solution of antigen is introduced and contacts the surface at a low temperature, followed by lyophilization to remove water, and the test tube contents are then protected by providing an inert atmosphere and sealing against external atmosphere.

16. A method for the immunochemical determination of a component of the antigen-antibody reaction which comprises:
   a. coating by adsorption at least a small portion of the internal surface of a test tube of water insoluble polymeric material with the component not to be determined, said water insoluble polymeric material being capable of sorbing said component;
   b. contacting the internal surface of said test tube with a buffered aqueous solution of protein to reduce the non-specific binding of the other component;
   c. contacting the internal surface of said test tube, cooled to a temperature between about -10° C and about 5° C, with the buffered sample containing the other component in labelled form capable of emitting radiation;
   d. freezing immediately the contents of said test tube;
   e. lyophilizing the contents of said test tube; and
   f. storing said test tube in the absence of air and water until required for use.

17. A method of determining a component of an antigen-antibody reaction in a sample solution which comprises coating and binding one of the components to at least part of a surface within a receptacle capable of binding said component and contacting the surface with the other component in labelled form in a manner to disperse it over the surface but not bound thereto, said components being retained within said receptacle under conditions substantially impervious to the ambient atmosphere, thereafter contacting the surface with a sample solution containing one of the components thereby producing a two-phase system and permitting interaction between the components causing some of the labelled component to be indirectly bonded to the surface, separating the two phases, and measuring the labelled content of one of the phases which is a function of the concentration of the component in the sample solution.

18. The method of claim 17 in which the labelled component in solution is quick-frozen upon contacting the surface followed by lyophilization to leave the labelled component as a solid residue on the surface.

19. The method of claim 17 in which part of the internal surface of a test tube of water-insoluble impervious polymeric material is coated with antibody from aqueous solution to bind antibody to its surface, followed by aspiration and washing, and an aqueous solution of labelled antigen is then introduced and contacts the surface at a low temperature no higher than about freezing temperature, followed by lyophilization to remove water, and storage under inert atmosphere prior to use.

20. The method of claim 19 in which the test tube is coated with protein prior to introduction of labelled antigen.

21. The method of claim 19 in which the test tube is composed of polyolefinic polymer and the antibody is adsorbed thereon.

22. The method of claim 19 in which a polystyrene tube is employed.

23. The method of claim 19 in which a sample solution of antigen is assayed and the quantity of bound antibody is insufficient to react with all of the labelled antigen and antigen in the sample solution.

24. A method for the immunochemical determination of a component of the antigen-antibody reaction which comprises:
   a. coating by adsorption at least a small portion of the internal surface of a test tube of water insoluble polymeric material with the component not to be determined, said water insoluble polymeric material being capable of sorbing said component;
   b. contacting the internal surface of said test tube with a buffered aqueous solution protein to reduce the non-specific binding of the other component;
   c. contacting the internal surface of said test tube, cooled to a temperature between about −10° C and about 5° C, with the buffered sample containing the other component in labelled form capable of emitting radiation;
   d. freezing immediately the contents of said test tube;
   e. lyophilizing the contents of said test tube;
   f. adding a sample containing the component to be determined to said test tube.
   g. allowing the immunochemical reaction to take place to produce a two-phase system, comprising a solid phase and a liquid phase, wherein said solid phase includes the bound part of the labelled and unlabelled component to be determined and the liquid phase includes the unbound labelled and unlabelled component to be determined;
   h. separating the solid phase from the liquid phase; and
   i. determining the activity of the solid phase, said activity being a function of the concentration of said component to be determined in said sample.

25. The method of claim 24 wherein the antibody is antidigoxin and the method is used to determine digoxin.

26. The method of claim 24 wherein the antibody is anticyclic adenosine monophosphate and the method is used to determine cyclic adenosine monophosphate.

27. The method of claim 24 wherein the antibody is antihuman growth hormone and the method is used to determine human growth hormone.

28. The method of claim 24 wherein the protein bound to the internal surface of the container is serum albumin.

29. The method of claim 24 wherein the component to be determined in labelled form is labelled with a radioactive isotope of iodine.

30. The method of claim 24 wherein the radioactive isotope is $I^{125}$.

31. The means of claim 1 in which the unbound component is labelled with a radioactive atom.

32. The means of claim 1 in which the unbound component is labelled with an enzyme.

33. The means of claim 1 in which the unbound component is labelled with a fluorescent group.

* * * * *